United States Patent [19]

Fisher et al.

[11] Patent Number: 4,672,081
[45] Date of Patent: Jun. 9, 1987

[54] IMPRESSION MATERIAL

[75] Inventors: Robert G. Fisher, Beckenham; Keith James, Carshalton; Graham M. Pring, Woking, all of England

[73] Assignee: The British Petroleum Company p.l.c., London, England

[21] Appl. No.: 776,165

[22] PCT Filed: Dec. 20, 1984

[86] PCT No.: PCT/GB84/00444
§ 371 Date: Sep. 10, 1985
§ 102(e) Date: Sep. 10, 1985

[87] PCT Pub. No.: WO85/03221
PCT Pub. Date: Aug. 1, 1985

[30] Foreign Application Priority Data

Jan. 18, 1984 [GB] United Kingdom ................ 8401236

[51] Int. Cl.[4] .......................... A61K 6/10; C08C 19/00
[52] U.S. Cl. ...................................... 523/109; 106/35; 433/214; 525/381; 525/382; 525/372.6
[58] Field of Search .......................... 523/109; 106/35; 433/214; 525/381, 382, 372.6

[56] References Cited

U.S. PATENT DOCUMENTS 4,341,716 7/1982 Diery et al. .................... 260/456 A

FOREIGN PATENT DOCUMENTS 2027035A 2/1980 United Kingdom .

Primary Examiner—John Kight
Assistant Examiner—M. L. Moore
Attorney, Agent, or Firm—Morgan & Finnegan

[57] ABSTRACT

A two part impression material suitable for use as a dental impression material comprises a first part containing a product of the reaction of an alpha, beta-ethylenically unsaturated dicarboxylic acid anhydride, such as maleic anhydride, and a liquid polydiene resin, e.g. polybutadiene, and a second part containing a setting agent for the reaction product which setting agent is an alkoxylated fatty mono-amine or an alkoxylated fatty polyamine having from 2 to 30, preferably 5 to 15 moles of alkoxylate per mole of the fatty amine. The alkoxylate groups of the setting agent being one or more groups selected from the group comprising ethoxylate, propoxylate and butoxylate groups. A method of taking a dental impression using the reaction product of the first and second parts of the two part dental impression material is also disclosed.

18 Claims, No Drawings

IMPRESSION MATERIAL

The present invention relates to a two part impression material, suitable for use as a dental impression material, to a method of preparing the impression material and to a process for using the two part impression material to obtain an impression.

British Pat. No. GB 2 027 035B discloses a two-part dental impression material comprising a first part containing a product of the reaction of an alpha, beta ethylenically unsaturated dicarboxylic acid anhydride and a liquid polydiene resin and a second part containing a setting agent which has at least two reactive hydrogen atoms per molecule and is capable of forming a cross-link between molecules of said reaction product. The patent states that suitable setting agents include amines, polyols, amides, alkanolamines and alkanolamides. Also included are polyepoxides in combination with an epoxide ring-opening or carboxylic anhydride ring-opening compound.

Some of the requirements of a dental impression material are indicated in the introduction of No. GB 2 027 035B and British Standard Specification No. BS 4269: Part 1: 1968 specifies a number of physical properties required by an elastomeric dental impression material.

It has now been found that the use of certain alkoxylated setting agents provides impression materials having improved performance as compared with the dental impression materials described in No. GB 2 087 035B. In particular, the use of the selected setting agents enables the impression materials to satisfy the criteria of No. BS 4269: Part 1: 1968.

Thus, according to the present invention a two part impression material, suitable for use as a dental impression material, comprising a first part containing a product of the reaction of an alpha, beta-ethylenically unsaturated dicarboxylic acid anhydride and a liquid polydiene resin and a second part containing a setting agent for the said reaction product is characterised in that the setting agent is an alkoxylated fatty monoamine or an alkoxylated fatty polyamine having from 2 to 30 moles of alkoxylate per mole of the fatty amine, the alkoxylate groups being one or more alkoxylates selected from the group comprising ethoxylate, propoxylate and butoxylate groups.

Although the two part impression material according to the present invention is particularly suitable for use as a dental impression material, it may be used in other applications. For example, the two part impression material may be used to take an impression of an ear for use in the fitting of hearing aids. Thus, although the invention will be described hereinafter with particular reference to its use as a dental impression material this should not be taken as limiting the invention to this application.

The present invention includes a method of preparing an impression material, particularly a dental impression material, which method comprises mixing together the two parts of the impression material as described above and also includes the product of the reaction between the first and second part of the impression material.

The invention also includes a method of taking a dental impression which comprises placing in a dental impression mould a dental impression material prepared by mixing together the two parts of the impression material as hereinbefore described, bringing the mould into contact with the patient's teeth or jaws or with a dental model or prosthesis, allowing the dental impression material to set and thereafter removing the mould to leave an impression in the dental impression material.

Alkoxylated monoamines and polyamines are known and some are commercially available. They may be prepared by alkoxylating fatty amines by known methods. The fatty amines are preferably derived from a $C_8$ to $C_{22}$ compound containing one or more saturated or unsaturated fatty acid. More preferably, the fatty amines are derived from $C_{12}$ to $C_{18}$ compounds such as, for example, oleic, lauric, palmitic or stearic acid, tallow or hydrogenated tallow, coconut oil or soya bean oil. The alkoxylate groups are preferably ethoxylate or propoxylate groups or mixtures thereof. Preferably the setting agents have from 5 to 15 moles of alkoxylate per mole of fatty amine.

Setting agents suitable for use in the compositions according to the present invention include alkoxylated fatty amines having the following general formula:

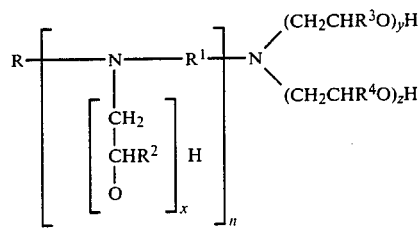

where
R is a hydrocarbyl group having from 8 to 22 carbon atoms
$R^1$ is $(CH_2)_3$ or $CH_2CH(CH_3)CH_2$
$R^2$, $R^3$ and $R^4$ are the same or different and are H, $CH_3$ or $CH_2CH_3$
n is 0 or a positive integer from 1 to 3
x, y and z are the same or different and are individually 0 or a positive integer from 1 to 6, the sum of x,y and z being from 2 to 30, preferably 5 to 15.

If x, y or z in the above formula is greater than 1, then the alkoxylate group may be a mixture of alkoxylates. For example, if y=3 then $(CH_2CHR^3)_y$ may comprise two ethoxylate groups and one propoxylate group.

The extent of alkoxylation is the number of moles of alkoxylate per mole of fatty amine i.e. in the above formula, the extent of alkoxylation of a monoamine is y+z and of a diamine is x+y+z. However, in practice an alkoxylated fatty amine is likely to be a mixture of amines. Thus, although x,y and z are given as integers or zero in the above formula, the extent of alkoxylation may not be an integer.

Suitable setting agents for use in the present invention include;
N,N-bis(11¹-hydroxy-3¹:6¹:9¹-trioxaundecyl)-octadec-9-enylamine
N,N¹,N¹-tris(11¹-hydroxy-2¹,5¹,8¹-trimethyl-3¹:6¹:9¹-trioxadodecyl)N-octadec-9¹¹-enyl-1,3-diaminopropane
N,N¹,N¹-tris(8¹-hydroxy-2¹,5¹-dimethyl-3¹:6¹-dioxanonyl) N-octadec-9¹¹-enyl-1,3-diaminopropane.

The most suitable alpha, beta-ethylenically unsaturated dicarboxylic acid anhydride for use in the preparation of the reaction product is maleic anhydride.

The liquid polydiene resin may be a homopolymer of a conjugated diene or a copolymer of a conjugated diene and one or more copolymerisable ethylenically unsaturated monomers. If the liquid polydiene resin is a copolymer, it preferably comprises at least 50% by weight of a conjugated diene. The polydiene resin may be prepared by known polymerisation methods.

The conjugated diene is preferably butadiene and an example of a suitable copolymerisable ethylenically unsaturated monomer is styrene.

The number average molecular weight of the liquid polydiene resin is preferably from 1,000 to 10,000.

The reaction of a liquid polydiene, such as polybutadiene, and an alpha, beta-ethylenically unsaturated dicarboxylic acid anhydride, such as maleic anhydride, is well known. A conventional method of preparing maleinised polydiene is disclosed in British Pat. No. GB 2 027 035B. The reaction between the liquid polydiene and the alpha-beta-ethylenically unsaturated dicarboxylic acid will be referred to as "functionalisation" in this specification and the reaction product will be referred to as "functionalised" polymer. Typically, the extent of functionalisation, e.g. the amount of maleic anhydride units associated with the polydiene, is from 5 to 20 parts by weight per 100 parts of the polydiene.

After functionalisation, the reaction product may be stripped by heating under vacuum to remove any traces of volatile material. A volatile solvent or diluent may be added to the functionalised polymer prior to the stripping step. The functionalised polymer may also be washed with a solvent with which it is immiscible, e.g. water, in order to remove soluble material. The final product preferably has a free maleic anhydride content of not more than 0.15% by weight.

Generally the first and/or second parts of the impression material according to the present invention contain fillers, plasticisers and other additives and are in the form of a paste. Conveniently both parts of the impression material are in the form of pastes, the viscosity of the pastes being such that the two parts may be easily mixed together. Mixing of the two parts is generally effected by hand using a spatula or similar tool. The two parts may be pigmented such that they have contrasting colours. This provides a means of visually indicating when a homogeneous mix is achieved.

The use of fillers in the first and/or second part of the impression material affects the viscosity of the part prior to mixing and confers the properties of opacity and/or toughness on the final impression material. The inclusion of fillers may also affect the rate of setting of the materials. As already mentioned, the viscosity of each part of the impression material should be such that the two parts may be easily mixed together and so the amount of filler used will be determined to some extent by the viscosities of the other components. Typically, the proportion of filler in either or both parts of the impression material is from 0 to 80% by weight and is conveniently from 10 to 70% by weight. The water content of the filler is preferably relatively low e.g. less than 0.1% by weight. A relatively high water content may adversely affect the storage stability of the product.

Suitable fillers include those conventionally used in dental impression materials such as for example whiting, china clay, ground limestone, barytes, talc and silica.

Conventional pigments and dyes, e.g. those known for use in dental materials, may be used to colour one or both parts of the impression material.

Diluents and plasticisers such as those conventionally used in polymer compositions may be included in either or both parts of the impression material.

One or both parts of the impression material may also contain a mould release agent such as, for example, silicone oil.

The relative proportions of the first and second parts which are mixed together to form the impression material depend on a number of factors such as, the amount of the setting agent in the second part and the amount of the functionalised polymer and its extent of functionalisation, the setting time required and the degree of cross-linking required. The relative proportions are generally selected such that there are at least sufficient active groups in the second part of the impression material containing the setting agent to react with all of the anhydride groups of the functionalised polymer in the first part. Preferably, however, the proportions are such that the amount of setting agent used is at least 1.5 times the stoichiometic amount required to react with all of the anhydride groups of the functionalised polymer. A practical upper limit is 4 times the stoichiometric amount. More preferably the amount of setting agent is from 1.75 to 2.25 times the stoichiometric amount required to react with all of the anhydride groups of the functionalised polymer. The use of more than the stoichiometric amount of setting agent improves the tension set of the final impression material.

The invention is illustrated by the following examples:

EXAMPLES 1 to 10

Various setting agents were mixed with maleinised polybutadiene. The setting agents were ethoxylated lauryl monoamines having different ethoxylate levels, propoxylated oleyl diaminopropanes having different propoxylate levels and ethoxylated coconut oil diaminopropanes having different ethoxylate levels. The maleinised polybutadiene used was a commercially available product sold under the trademark LITHENE LX16 10MA by Revertex Limited which contained 10 parts by weight of maleic anhydride per 100 parts by weight of polybutadiene; the polybutadiene having a molecular weight of approximately 8000.

In each case, sufficient setting agent was mixed with the maleinised polybutadiene to react with substantially all of the anhydride groups of the functionalised polymer.

The components were easily mixed together using a spatula to produce a homogeneous blend.

The working time of each composition was determined. This was done by measuring the time from the start of mixing to the commencement of setting. The commencement of setting was taken to be the point at which a filament could not be drawn out of the mixture with a spatula. The IRHD hardness of some of the compositions was measured 10 mins and 30 mins from the start of mixing.

The results given in Table 1 show that for any particular fatty amine, increasing the alkoxylate level increases the working time, but tends to reduce the hardness.

The compositions of Examples 2, 3, 5, 8, 9 and 10 have working times which are not less than the minimum working time specified in BS 4269. The other examples are included to show how the working time varies with alkoxylate level. Impression materials having working times less than the minimum specified in BS 4269 may have uses in applications other than for dental impressions.

TABLE 1
Effect of Alkoxylate Level on Working Time and Hardness

| Example | Setting Agent | Extent of Alkoxylation | Working Time (mins) | Hardness (Minutes from mixing time) 10 | Hardness (Minutes from mixing time) 20 |
|---|---|---|---|---|---|
| 1 | Ethoxylated lauryl monoamine | 5 | 1.0 | 35 | 52 |
| 2 | " | 10 | 2.8 | 28 | 43 |
| 3 | " | 15 | 3.7 | 28 | 34 |
| 4 | Ethoxylated coconut oil diamino propane | 15 | 1.1 | 42 | 60 |
| 5 | " | 20 | 1.5 | 42 | 56 |
| 6 | Propoxylated oleyl diamino propane | 3 | 0.58 | | |
| 7 | " | 7 | 1.08 | | |
| 8 | " | 8 | 1.25 | | |
| 9 | " | 9 | 1.42 | | |
| 10 | " | 12 | 2.10 | | |

EXAMPLES 11 to 20

Examples 1 to 10 were repeated except that the maleinised polybutadiene used was Lithene N₄ 5000 1OMA ex Revertex Limited. The polybutadiene of this material has a molecular weight of approximately 5000. The working times for these compositions are given in Table 2 and show, by comparison with the results given in Table 1, that a reduction in the molecular weight of the polydiene increases the working time.

TABLE 2
Effect of polydiene molecular weight on working time

| Example | Setting Agent | Extent of Alkoxylation | Working Time (mins) |
|---|---|---|---|
| 11 | Ethoxylated lauryl monoamine | 5 | 1.3 |
| 12 | Ethoxylated lauryl monoamine | 10 | 3.6 |
| 13 | Ethoxylated lauryl monoamine | 15 | 4.8 |
| 14 | Ethoxylated coconut oil diamino propane | 15 | 1.2 |
| 15 | Ethoxylated coconut oil diamino propane | 20 | 1.8 |
| 16 | Propoxylated oleyl diamino propane | 3 | 0.83 |
| 17 | Propoxylated oleyl diamino propane | 7 | 1.67 |
| 18 | Propoxylated oleyl diamino propane | 8 | 1.92 |
| 19 | Propoxylated oleyl diamino propane | 9 | 2.33 |
| 20 | Propoxylated oleyl diamino propane | 12 | 4.0 |

EXAMPLES 21 TO 25

Different fillers were mixed with maleinised polybutadiene, Lithene N₄ 5000 10MA. An ethoxylated oleyl monoamine setting agent having an ethoxylate level of 8 was then added to each polymer/filler mixture and the working time and hardness of each composition determined as in Examples 1 to 10. The results are given in Table 3.

TABLE 3

| Example | Filler | Amount of Filler (% wt/wt) | Working Time (mins) | Hardness (Mins after mixing time) 10 | Hardness (Mins after mixing time) 30 |
|---|---|---|---|---|---|
| 21 | Calcium carbonate | 25 | 3.25 | 34 | 65 |
| | Talc | 25 | | | |
| 22 | Glass microspheres | 7 | 3.2 | 29 | 38 |
| 23 | Micronised polypropylene | 22 | 3.8 | 28 | 28 |
| 24 | China clay | 24 | 4.0 | 28 | 38 |
| 25 | Microsilica | 12 | 3.5 | 28 | 34 |

EXAMPLE 26

A two part dental impression material according to the present invention was prepared by mixing together the following components to form a first part and a second part:

| | Parts by weight |
|---|---|
| First Part | |
| Maleinised polybutadiene | 46 |
| Filler | 41 |
| Release agent | 10 |
| Plasticiser | 3 |
| Second Part | |
| Alkoxylated fatty amine | 50 |
| Filler | 50 |
| Dye | 0.025 |

The maleinised polybutadiene used was the reaction product of maleic anhydride and liquid polybutadiene sold by Revertex Limited under the designation LITHENE LX16 10MA (LITHENE is a trademark). The molecular weight of the polybutadiene was approximately 8000 and the polymer contained 10 parts by weight of maleic anhydride per 100 parts by weight of polybutadiene.

The filler included in the first part of the composition was ground dolomite sold under the trade mark MICRODOL Extra by Norwegian Talc (UK) Ltd. The filler had a moisture content of approximately 0.05% by weight.

The release agent used was a silicone fluid sold by Dow Corning Ltd under the designation DC 550.

The plasticiser was a dioctyl adipate sold by BP Chemicals Limited under the trade name BISOFLEX DOA (BISOFLEX is a registered trade mark).

The alkoxylated fatty amine was a propoxylated oleyl diamino propane. The extent of propoxylation i.e. the number of moles of propoxylate per mole of oleyl diaminopropane was 12±0.4.

The filler used in the second part of the composition was calcium carbonate sold under the trade name CALOFORT S by John & E Sturge Limited.

The dye used to colour the second part of the composition was an oil soluble red dye having the colour index (1971) reference Solvent Red 23 No 26100. The first part of the composition had a viscosity of 180 PaS at 25° C.

The first part and second part were mixed together in the volume ratio of 2:1. These proportions provided 1.77 times the stoichiometric amount of setting agent required to react with all of the anhydride groups of the maleinised polybutadiene.

The properties of the mixed composition were as follows:
- Working time: 4 mins
- Setting time: 10 mins
- Tension set: 2.5%
- Elongation: at break: 230%
- Dimensional stability: 0.1%
- International Rubber Hardness: (30 mins) 40

The properties were determined according to BS4269:Part 1 1968 except for the International Rubber Hardness which was determined according to ASTM D 1415-68.

The working time and setting time were within the limits set by BS4269 for a regular set material. The tension set was also acceptable in terms of the limits set by the British Standard for polysulphide dental impression materials.

The British Standard states that the elongation at break of the material should be greater than 50% and the dimensional stability should be not more than ±0.2%. Thus the impression material according to the present invention had the properties of an acceptable dental impression material as defined by BS 4269.

EXAMPLE 27

A two part dental impression material was prepared substantially as described in Example 26 except that the proportions of the components of the first part of the composition were;
- Maleinised polybutadiene: 46
- Filler: 47
- Release agent: 5
- Plasticiser: 2

The setting agent used in the second part of the impression material was based on a commerically available fatty amine and was a propoxylated oleyl diaminopropane alkoxylated to a level of approximately 10.5 to 11.0. Apart from this, the second part of the impression material was as for Example 26.

The first part had a viscosity of 340 Pa.s at 25° C. The first part and second part were mixed together in the volume ratio of approximately 2:1. These proportions provided approximately 1.9 times the stoichiometric amount of setting agent required to react with all of the anhydride groups of the maleinised polybutadiene. The impression material was found to have the following properties.
- Working time: 2.5 mins
- Setting time: 6 mins
- Tension set: 1.5%
- Elongation at break: 190%
- Dimensional stability: 0.1%
- International Rubber Hardness: (30 mins) 35

This composition was less fluid than the composition according to example 26 and was somewhat easier to handle.

The impression material had a working time and setting time within the limits set by BS 4269 for a regular set material and as for Example 26, the tension set, elongation at break and dimensional stability were well within the limits set by the British Standard.

A dental impression was successfully obtained using this composition. After washing and drying the impression it was filled with dental plaster and a cast obtained.

EXAMPLE 28

A two part dental impression material was prepared as described in Example 27 except that the alkoxylated fatty amine setting agent used in the second part of the composition had a level of propoxylation of 9.0±0.4 rather than 12 or 10.5 to 11.0 as in Examples 26 and 27.

When the first part, which was the same as for Example 27, and the modified second part were mixed together in the volume ratio of approximately 2:1. These proportions provided approximately 2.13 times the stoichiometric amount of the setting agent required to react with all of the anhydride groups of the maleinised polybutadiene. The impression material was found to have the following properties:
- Working time: 1.7 mins
- Setting time: 5.25 mins
- Tension set: 1 to 1.5%
- Elongation at break: 150%
- Dimensional stability: 0.04%
- International Rubber Hardness: (30 mins) 36

The working time and setting time were faster than for Example 27 and the material would be a quick set material. The tension set, elongation at break and dimensional stability were once again well within the limits set by the British Standard.

A dental impression was sucessfully obtained using the composition and a plaster cast was made from the impression. The dental impression was then copper plated using conventional techniques. A plaster cast was taken from the copper plated impression and the copper was successfully transferred to the plaster cast.

By adding 10% by weight of additional plasticiser to the composition, a syringeable dental impression material was obtained which had a useable time of up to 1.6 min and a set time of 5.5 minutes.

EXAMPLE 29

A two part dental impression material according to the present invention was prepared comprising:

|  | Parts by weight |
| --- | --- |
| First Part |  |
| Maleinised polybutadiene | 45.3 |
| Filler | 42.1 |
| Release agent | 7.8 |
| Plasticiser | 4.8 |
| Second Part |  |
| Alkoxylated fatty amine | 50.0 |
| Filler | 50.0 |
| Dye | 1.0 |

The maleinised polybutadiene, fillers, release agent and plasticiser were the same as those used in Example 26. The alkoxylated fatty axine was the same as that used in Example 28. The dye was Red No 30 Lake.

The first part and second part were mixed together in the volume ratio of 2:1. These proportions provided approximately 2.16 times the stoichiometric amount of the setting agent required to react with all of the anhydride groups of the maleinised polybutadiene. The impression material had the following properties.
- Working time: 2.3 mins
- Setting time: 5.5 mins
- Tension set: 2.0–1.5
- Elongation at break: 210
- International Rubber Hardness: 30

This impression material was successfully used as a syringeable grade dental impression material and was also used, without modification, in a dental tray to prepare a dental impression.

We claim:

1. A two part impression material, suitable for use as a dental impression material, comprising a first part containing a product of the reaction of an alpha,beta-ethylenically unsaturated dicarboxylic acid anhydride and a liquid polydiene resin, and a second part containing a setting agent for the said reaction product, characterised in that the setting agent is an alkoxylated fatty mono-amine or an alkoxylated fatty polyamine having from two to thirty moles of alkoxylate per mole of the fatty amine, the alkoxylate groups being one or more alkoxylates selected from the group comprising ethoxylate, propoxylate and butoxylate groups.

2. An impression material as claimed in claim 1 in which the setting agent is derived from a composition comprising one or more saturated or unsaturated fatty acids having from 12 to 18 carbon atoms.

3. An impression material as claimed in claim 2 in which the setting agent is derived from one or more compositions selected from the group comprising oleic acid, lauric acid, palmitic acid, stearic acid, tallow acid, hydrogenated tallow acid, coconut oil and soya bean oil.

4. An impression material as claimed in any of claims 1 to 3 in which the alkoxylate groups of the setting agent are ethoxylate groups, propoxylate groups or mixtures thereof.

5. An impression material as claimed in any of claims 1 to 4 in which the setting agent is an alkoxylated mono-amine or polyamine having from 5 to 15 moles of alkoxylate per mole of fatty amine.

6. An impression material as claimed in any of claims 1 to 5 in which the setting agent is an alkoxylated mono- or poly- amine having the general formula;

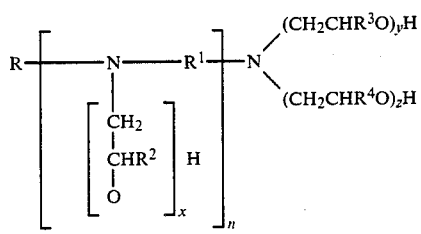

where

R is a $C_8$ to $C_{22}$ hydrocarbyl group, $R_1$ is $(CH_2)_3$ or $CH_2 CH(CH_3)CH_2$, $R_2$, $R_3$ and $R_4$ are the same or different and are selected from H, $CH_3$, and $CH_3CH_2$ n is 0 or a positive integer from 1 to 3 and x,y and z are the same or different and are individually 0 or a positive integer from 1 to 6, the sum of x,y and z being from 2 to 30.

7. An impression material as claimed in claim 6 in which the setting agent is $N,N^1,N^1$-tris($8^1$-hydroxy-$2^1,5^1$-dimethyl-$3^1$:$6^1$-dioxanonyl)N-octadec-$9^{11}$-enyl-1,3-diaminopropane.

8. An impression material as claimed in any of claims 1 to 7 in which the first part contains a product of the reaction of maleic anhydride and a homopolymer or copolymer of polybutadiene.

9. An impression material as claimed in claim 8 in which the reaction product comprises from 5 to 20 parts by weight of maleic anhydride per 100 parts of the polybutadiene.

10. An impression material as claimed in any of claims 1 to 8 wherein the first part and/or second part is in the form of a paste and contains up to 80% by weight of filler.

11. A two part impression material, suitable for use as a dental impression material, according to claim 1 in which the first part comprises (a) maleinised polybutadiene, (b) a filler, (c) a release agent and (d) a plasticiser and the second part comprises (a) a propoxylated oleyl diaminopropane, propoxylated to a level of from 5 to 15 and (b) a filler.

12. A method of preparing an impression material, suitable for use in taking dental impressions, comprises mixing together the first part and the second part of the two part impression material as claimed in any of claims 1 to 11.

13. A method as claimed in claim 12 in which the amount of the second part mixed with the first part is such that the amount of setting agent is from 1.5 to 4 times the stoichiometric amount required to react with all of the anhydride groups of the reaction product of the first part.

14. A method as claimed in claim 13 in which the amount of the second part mixed with the first part is such that the amount of setting agent is from 1.75 to 2.25 times the stoichiometric required to react with all of the anhydride groups of the reaction product of the first part.

15. An impression material, suitable for use as a dental impression material, comprising the product of the reaction between the first part and the second part of a two part dental impression material as claimed in any of claims 1 to 11.

16. An impression material as claimed in claim 15 which is the product of the reaction between the first part and an amount of the second part which contains from 1.5 times to 4 times the stoichiometric amount of setting agent required to react with all of the anhydride groups of the reaction product in the first part.

17. An impression material as claimed in claim 16 which is the product of the reaction between the first part and an amount of the second part which contains from 1.75 times to 2.25 times the stoichiometric amount of setting agent required to react with all of the anhydride groups of the reaction product in the first part.

18. A method of taking a dental impression which comprises placing in a dental impression mould an impression material prepared according to the method as claimed in any of claims 12 to 14, bringing the mould into contact with the patient's teeth, or jaws or with a dental model or prosthesis, allowing the dental impression material to set and thereafter removing the mould to leave a impression in the dental impression material.

* * * * *